United States Patent [19]
Kitajima

[11] Patent Number: 5,835,266
[45] Date of Patent: *Nov. 10, 1998

[54] MEDICAL MICROSCOPIC SYSTEM

[75] Inventor: Nobuaki Kitajima, Tokyo, Japan

[73] Assignee: Kabushiki Kaisha Topcon, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 782,559

[22] Filed: Jan. 10, 1997

Related U.S. Application Data

[63] Continuation of Ser. No. 518,228, Aug. 23, 1995, abandoned, which is a continuation of Ser. No. 86,705, Jul. 7, 1993, abandoned.

[30] Foreign Application Priority Data

Jul. 8, 1992 [JP] Japan .................................. 4-181186

[51] Int. Cl.$^6$ .......................... G02B 21/00; G02B 21/36
[52] U.S. Cl. ........................ 359/384; 359/363; 359/368
[58] Field of Search ................................ 359/362, 363, 359/368, 372–384, 689; 351/205–208, 211–214, 221; 348/72–76, 79–80, 159; 250/201.2–201.4

[56] References Cited

U.S. PATENT DOCUMENTS

| 3,566,872 | 3/1971 | Draeger et al. | 359/384 |
|---|---|---|---|
| 4,155,622 | 5/1979 | Klein | 359/379 |
| 4,443,076 | 4/1984 | Itabashi | 359/380 |
| 4,594,608 | 6/1986 | Hatae et al. | 359/363 |
| 4,812,033 | 3/1989 | Ishikawa | 351/208 |
| 4,871,245 | 10/1989 | Ishikawa et al. | 359/388 |
| 4,912,388 | 3/1990 | Tanaka et al. | 359/382 |
| 5,006,872 | 4/1991 | Parker | 359/363 |
| 5,074,651 | 12/1991 | Nagamine | 389/384 |
| 5,157,552 | 10/1992 | Hagimori | 359/689 |

FOREIGN PATENT DOCUMENTS

| 81715 | 4/1991 | Japan | 359/380 |
|---|---|---|---|

*Primary Examiner*—Thong Nguyen
*Attorney, Agent, or Firm*—Finnegan, Henderson, Farabow, Garrett & Dunner, L.L.P.

[57] ABSTRACT

A medical microscopic system includes an observation optical system for observing an image of a part to be observed, an electronic photographing optical system for branching a beam of light incident on the observation optical system from the observation part by a beam splitter disposed in an optical path of the observation optical system and then guiding its branched beam of light to a TV camera disposed conjugate with the observation part, and an adapter lens, disposed in an optical path between the observation part and the TV camera, for changing an optical path length which causes the TV camera and the observation part to be conjugate with each other.

13 Claims, 10 Drawing Sheets

MEDICAL MICROSCOPIC SYSTEM

This application is a continuatoin of aplication Ser. No. 08/518,228, filed Aug. 23, 1995, now abandoned; which is a continuation of application Ser. No. 08/086,705, filed Jul. 7, 1993, now abandoned.

BACKGROUND OF THE INVENTION

1. Field of the Invention

This invention relates to a medical microscopic system including an electronic photographing means.

2. Description of the Prior Art

In recent years, a medical stereo-microscope is widely used to perform a fine operation. However, there are also some cases where such an operation can be easily performed without the stereo-microscope.

On the other hand, it is widely carried out that such a fine operation is photographed with a TV camera and displayed on a monitor TV and further recorded on a VTR for education or presentation of a report on it at a meeting of a learned society. An example of an operating system for performing such photographing and recording as mentioned above is shown in FIG. 12. This figure shows that an operator 1 is performing an operation with a binocular stereo-microscope 3 fixed to a supporting structure 2 in an operating room.

The supporting structure 2 is constructed so that a supporting post 5 disposed in a cylindrical column 4 is free to move up and down by, for example, oil pressure, an arm shaft 6 mounted on the upper end of the supporting post 5 is free to move horizontally, and a supporting arm 7 joined to the arm shaft 6 is free to pivot as shown by the arrow 8. The binocular stereo-microscope 3 is fixed to the free end of the supporting arm 7.

The binocular stereo-microscope 3 generally includes an observation optical system for observing an image of a part to be observed and an electronic photographing optical system for branching a beam of light incident on the observation optical system from the observation part by a light branching means disposed in an optical path of the observation optical system and then guiding the branched beam of light to a solid state photographing device (electronic photographing means) of a TV camera (not shown). The image of the observation part photographed by the TV camera is recorded on the VTR 10 via a selector 9 and displayed on the monitor TV 11.

A shadow-free operating lamp 13 provided with a TV camera 14 is fixed to the ceiling 12 of the operating room. The image of the observation part photographed by this TV camera 14 is recorded on the VTR 10 via a selector 9 and displayed on the monitor TV 11. If the operation is performed without the binocular stereo-microscope 3, the supporting arm 7 is horizontally moved to clear the microscope 3 from an area above the observation part and to photograph the observation part with the TV camera 14.

However, it is economically disadvantageous to use both the TV camera (not shown) fixed to the microscope 3 and the TV camera fixed to the operating lamp 13.

Further, it is troublesome to switch those TV cameras by means of the selector 9 hand-operatedly.

SUMMARY OF THE INVENTION

It is therefore a first object of the invention to provide a medical stereo-microscope capable of taking an image of a high power and short operating distance and an image of a low power and long operating distance by a single electronic photographing means.

It is a second object of the invention to provide a medical stereo-microscope capable of automatically switching photography for the image of the high power and short operating distance to photography for the image of the low power and long operating distance, and vice versa.

To achieve the first object, one embodiment of the invention is characterized in that a medical microscopic system comprising an observation optical system for observing an image of a part to be observed, and an electronic photographing optical system for branching a beam of light incident on the observation optical system from the observation part by a branching means disposed in an optical path of the observation optical system and then guiding its branched beam of light to an electronic photographing means disposed conjugate with the observation part, further comprises a means, disposed in an optical path between the observation part and the electronic photographing means, for changing an optical path length which causes the electronic photographing means and the observation part to be conjugate with each other.

In this embodiment of the invention, the optical path length changing means is an adapter lens capable of changing a back focal distance. Further, the adapter lens comprises a front group of lenses and a back group of lenses, at least one of the front and back groups being moved so as to consecutively change a back focal distance. Further, the optical path length changing means is an adapter lens disposed between the observation part and an objective lens and fixed removably to an operation microscope. Further, a V-shaped groove is circularly formed around the lower portion of a holder of the microscope, the adapter lens comprising a ring-like adapter frame and a lens fitted therein, the adapter frame being fitted on the lower portion of the holder, a locking screw spiraled up from the adapter frame being engaged with the V-shaped groove so that the adapter lens is fixed removably to the microscope. Further, the optical path length changing means is a varifocal lens comprising a plurality of lenses and disposed in an optical path of the electronic photographing optical system. Further, the varifocal lens is moved in the direction of an optical axis by a moving device.

To achieve the second object, another embodiment of the invention is characterized in that a medical microscopic system comprising an operation microscope including an observation optical system for observing an image of a part to be observed, and an electronic photographing optical system for branching a beam of light incident on the observation optical system from the observation part by a branching means disposed in an optical path of the observation optical system and then guiding its branched beam of light to an electronic photographing means, the electronic photographing means being disposed conjugate with the observation part; and a supporting arm for supporting the microscope; further comprises a means, disposed in an optical path between the observation part and the electronic photographing means, for changing an optical path length which causes the electronic photographing means and the observation part to be conjugate with each other; a means for detecting a position of the supporting arm; and a control circuit for controlling the optical path length changing means based on a signal set from the detecting means.

In this embodiment of the invention, the optical path length changing means is an adapter lens capable of changing a back focal distance.

To achieve the second object, a further embodiment of the invention is characterized in that a medical microscopic system comprising: an operation microscope including an observation optical system for observing an image of a part to be observed, and an electronic photographing optical system for branching a beam of light incident on the observation optical system from the observation part by a branching means disposed in an optical path of the observation optical system and then guiding its branched beam of light to a first electronic photographing means disposed conjugate with the observation part; a supporting arm for supporting the microscope; a second electronic photographing means disposed on the side of the ceiling of an operating room; and a processing unit for processing image signals sent from the first and second photographing means; further comprises: a detecting means for detecting a position of the supporting arm; and a control circuit for switching the image signals sent from the first and second photographing means based on a detection signal of the detecting means and inputting either of the image signals to the image signal processing unit.

In this embodiment of the invention, the detecting means is a means for detecting a position of the supporting arm in an upward and downward direction of its movement. Further, the supporting arm is fixed to a supporting member so as to pivot on the end of the supporting arm and the position detecting means is disposed between the end and the supporting member. Further, the supporting arm is an articulated arm consisting of a plurality of arm segments each of which is free to pivot on a joint, the supporting arm being mounted on a supporting post so as to move horizontally, each joint of the arm segments being provided with a detecting means for finding a position of the supporting arm from an amount of movement of each arm segment. Further, the detecting means is a rotary encoder or potentiometer. Further, the supporting post is controlled to move upward and downward by a supporting post driving apparatus which is controlled by a control circuit receiving an operating signal of a foot switch. Further, the control circuit controls the supporting post driving apparatus to raise the supporting post so that the operation microscope moves upward by a given distance for coarse adjustment when the foot switch is turned on, while the control circuit controls the supporting post driving apparatus to lower the supporting post so that the operation microscope moves downward by a given distance for coarse adjustment when the foot switch is turned off. Further, the microscope is joined to the supporting arm so that the microscope is slightly raised or lowered by a fine adjustment and also the microscope is raised or lowered by a given distance by turning on or off the foot switch. Further, how much a coarse adjustment shifted the microscope is detected after a given time has elapsed since a foot switch was turned on, and then the first and second photographing means are switched based on a detected amount of movement of the microscope.

To achieve the second object, another embodiment of the invention is characterized in that a medical microscopic system comprising: an operation microscope including an observation optical system for observing an image of a part to be observed, and an electronic photographing optical system for branching a beam of light incident on the observation optical system from the observation part by a branching means disposed in an optical path of the observation optical system and guiding its branched beam of light to a first electronic photographing means disposed conjugate with the observation part; a supporting arm for supporting the microscope; a second electronic photographing means disposed on the side of the ceiling of an operating room; and a processing unit for processing image signals sent from the first and second photographing means; further comprises: a driving apparatus, joined to the supporting arm, for raising and lowering the microscope; and a control circuit for, based on a driving signal of the driving apparatus, switching an image signal sent from the first photographing means to an image signal sent from the second photographing means and inputting the latter image signal to the image signal processing unit so that the whole of the observation part can be displayed and for, based on another driving signal of the driving apparatus, switching an image signal sent from the second photographing means to an image signal sent from the first photographing means and inputting the latter image signal to the image signal processing unit so that a magnified image of the observation part can be displayed.

To achieve the second object, another embodiment of the invention is characterized in that a medical microscopic system comprising: an operation microscope including an observation optical system for observing an image of a part to be observed, and an electronic photographing optical system for branching a beam of light incident on the observation optical system from the observation part by a branching means disposed in an optical path of the observation optical system and guiding its branched beam of light to a first electronic photographing means disposed conjugate with the observation part; a supporting arm for supporting the microscope; a second electronic photographing means disposed on the side of the ceiling of an operating room; and a processing unit for processing image signals sent from the first and second photographing means; further comprises: a fine adjustment, joined to the supporting arm, for adjusting the microscope finely; a post for supporting and moving the supporting arm upward and downward; a coarse adjustment for moving the post upward and downward to adjust the microscope coarsely; a foot switch for operating the coarse adjustment; and a control circuit for, based on an on-off signal of the foot switch, switching an image signal sent from the first photographing means to an image signal sent from the second photographing means and inputting the latter image signal to the image signal processing unit so that the whole of the observation part can be displayed and for, based on another on-off signal of the foot switch, switching an image signal sent from the second photographing means to an image signal sent from the first photographing means and inputting the latter image signal to the image signal processing unit so that a magnified image of the observation part can be displayed.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the sprit of the invention or the scope of claims appended hereto.

BRIEF DESCRIPTION OF THE ATTACHED DRAWINGS

DESCRIPTION OF THE PREFERRED EMBODIMENTS

Embodiments of this invention will now be described with reference to FIGS. 1 through 11.

(First Embodiment)

Figure 1:
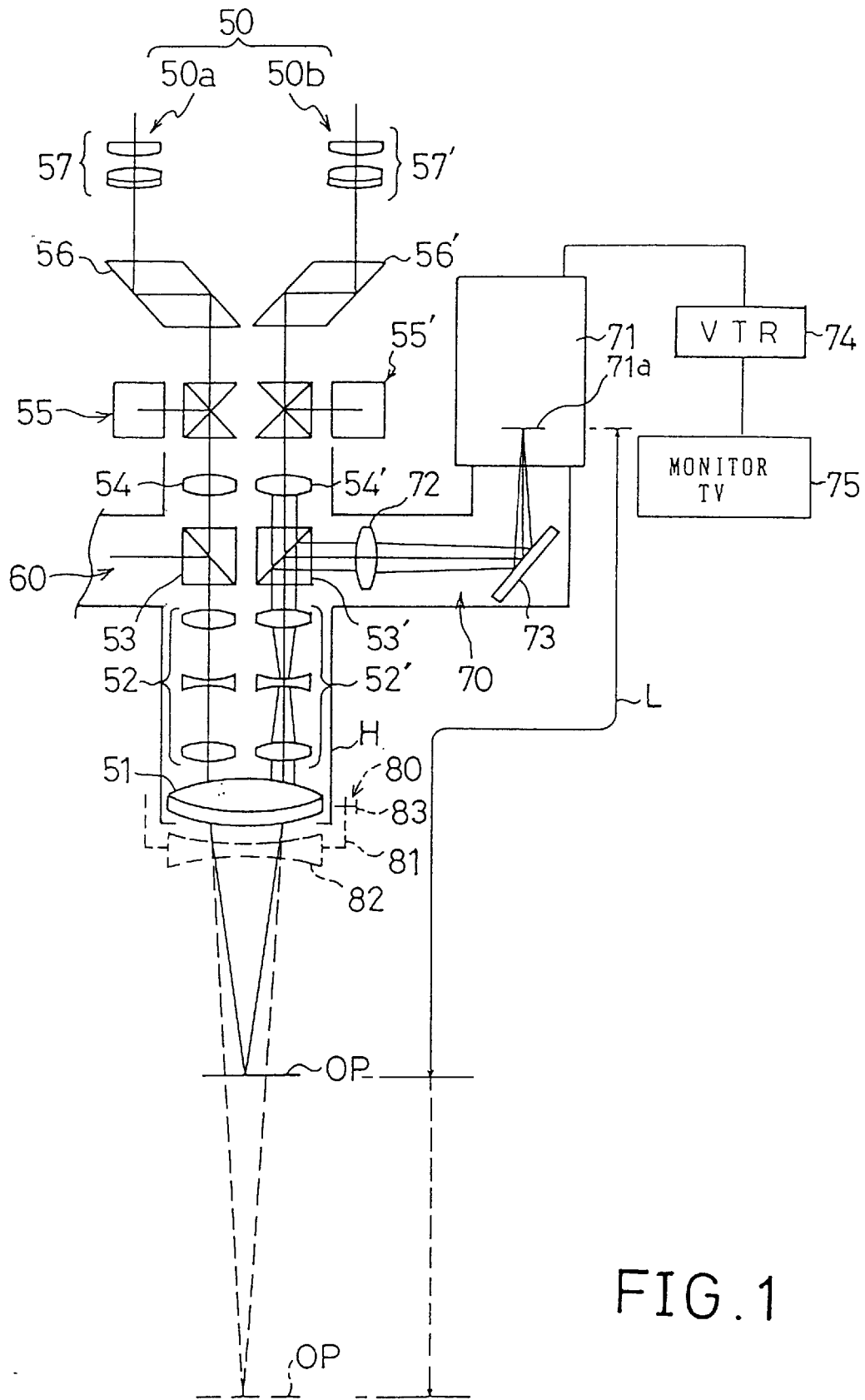
FIG. 1 is a descriptive drawing of the optical system of a first embodiment of a medical microscopic system according to the invention.
Figure 2:
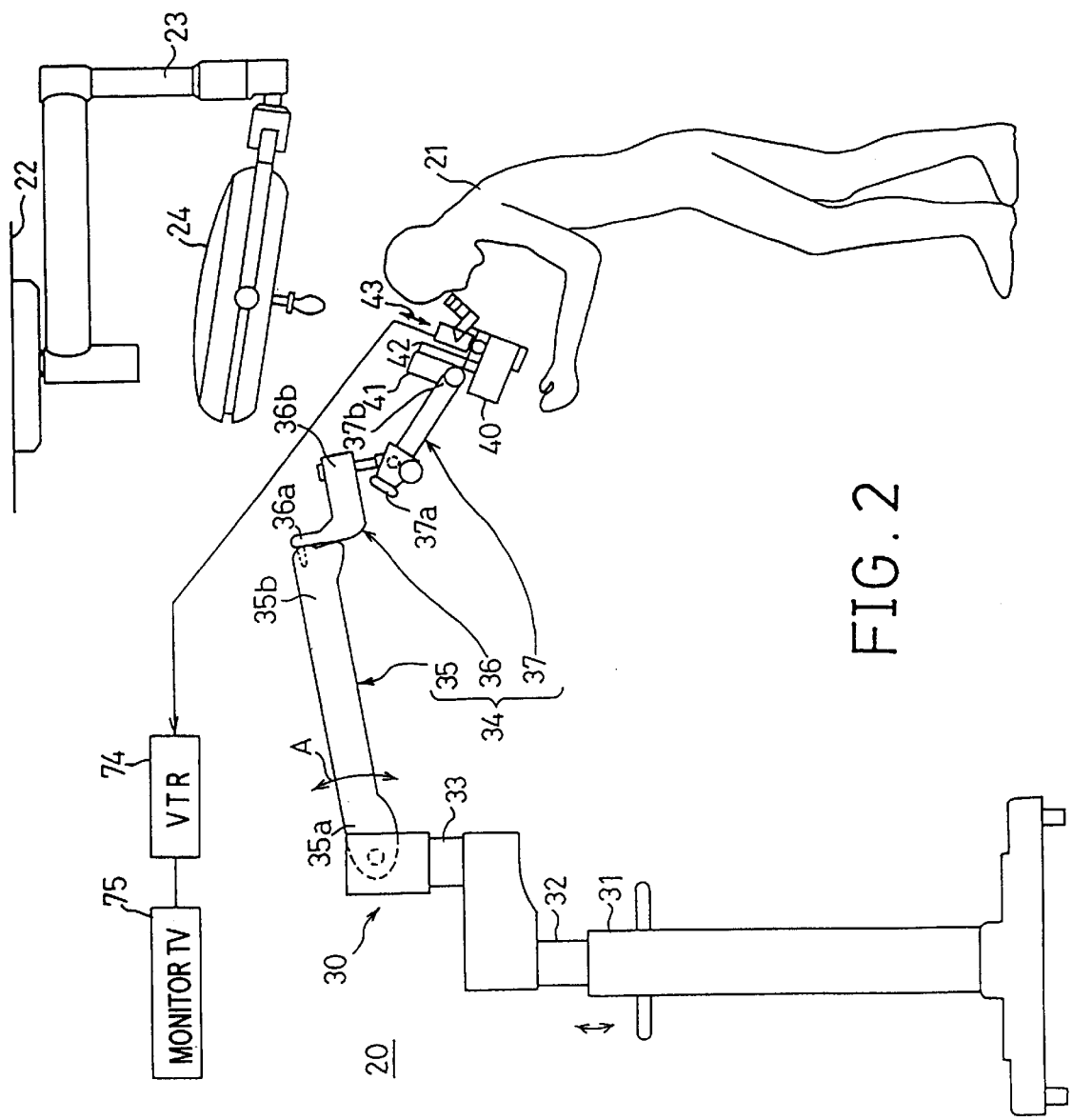
FIG. 2 is a schematic view of an operating room in which the medical microscopic system of FIG. 1 is set.
Figure 3:
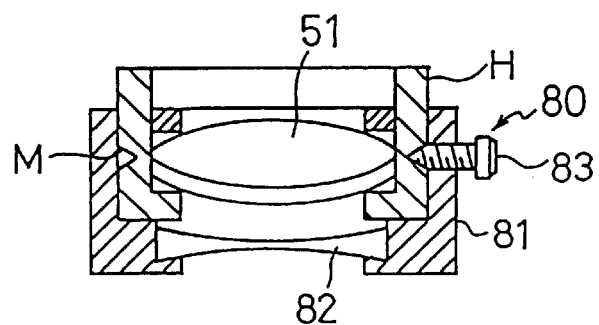
FIG. 3 is a partially enlarged descriptive drawing of the optical system of FIG. 1.

FIGS. 1 through 3 each show a first embodiment of the invention. Referring to FIG. 2, an operator 21 is performing an operation by using a binocular stereo-microscope 40 (that is, an operation microscope) fixed to a supporting apparatus 30 in an operating room 20. An L-shaped arm 23 is fixed to the ceiling 22 of the room 20 so as to move horizontally. A shadow-free operating lamp 24 is connected to the lower end of the arm 23.

The supporting apparatus 30 comprises a cylindrical supporting column 31, a supporting post 32 slidable inside the column by oil or air pressure, an arm shaft 33 mounted on the upper portion of the supporting post 32 so as to move horizontally, and a supporting arm 34 mounted on the arm shaft 33. The supporting arm 34 comprises an arm segment 35, one end 35a of which is joined to the arm shaft 33 so that the arm segment 35 can pivot upon the end 35a in the direction of the arrow A, an L-shaped arm segment 36, one end 36a of which is joined to the free end 35b of the arm segment 35 so that the L-shaped arm segment 36 can pivot upon the end 36a within a plane perpendicular to the lengthwise direction of the arm segment 35, and an arm segment 37, one end 37a of which is joined to the other end 36b of the arm segment 36 so that the arm segment 37 can pivot upon the end 37a.

A fine adjustment 41 including a motor and a mechanical reduction gear is joined to the free end 37b of the arm 37 so as to move in the same direction as the movement of the arm segment 36. A rising and falling member 42 is mounted on the fine adjustment 41 so as to move in the direction of the arrow 43 by means of the motor and the mechanical reduction gear. The rising and falling member 42 is fixed to the binocular stereo-microscope 40.

As shown in FIG. 1, the binocular stereo-microscope 40 includes a main observation optical system 50 for observing an image of an observation part OP. The main observation optical system 50 includes a left-hand/right-hand pair of optical systems 50a and 50b. The optical system 50a includes an objective lens 51, a variable power lens 52, a beam splitter (light branching means) 53, an imaging lens 54, a porro prism (image erecting prism) 55, a diamond-shaped prism (pupil distance adjusting means) 56, and an eyepiece 57 in that order. A light beam from the observation part OP, such as a part undergoing an operation, is guided to the eye of the operator 21 via the objective lens 51, the variable power lens 52, the beam splitter (light branching means) 53, the imaging lens 54, the porro prism (image erecting prism) 55, the diamond-shaped prism (pupil distance adjusting means) 56, and the eyepiece 57.

The objective lens 51, the variable power lens 52, the beam splitter (light branching means) 53, and the imaging lens 54 are housed in a holder H. As shown in FIG. 3, a groove M is formed around the lower portion of the holder H. Since the optical system 50b has the same composition as the optical system 50a, its description will be omitted, parts of the system 50b corresponding to parts of the system 50a being referred to by the same symbols with dashes (').

Further, the medical stereo-microscope 40 includes a sub optical system 60 for branching the light beam incident on the main observation optical system 50 from the observation part OP by means of the beam splitter 53 disposed in an optical path of the main observation optical system 50 and guiding a branched light beam to an observation optical system for an assistant.

Further, the medical stereo-microscope 40 includes an electronic photographing optical system 70 for branching the light beam incident on the main observation optical system 50 from the observation part OP by means of a beam splitter 53' disposed in an optical path of the main observation optical system 50 and guiding a branched light beam to a solid state photographing device (electronic photographing means) 71a of a TV camera 71. The electronic photographing optical system 70 includes the beam splitter 53', an imaging lens 72, and an oblique mirror 73. The solid state device 71a is disposed conjugate with the observation part OP. Therefore, the light beam incident on the optical system 50 from the observation part OP is branched off and guided to the solid state device 71a via the imaging lens 72 and the oblique mirror 73, so that an image of the observation part OP is formed on the solid state device 71a. An image signal sent from the solid state device 71a is input to a monitor TV 75 via a VTR 74 and the image of the observation part OP is displayed on the monitor TV 75.

Further, the medical stereo-microscope 40 includes an adapter lens 80 (optical path length changing means) for lengthening (changing) an optical path length L which causes the solid state device 71a and the observation part OP to be conjugate with each other. The adapter lens 80 is made up of a ring-like adapter frame 81, a concave lens 82 fitted in the adapter frame 81, and a locking screw 83 piercing through the adapter frame 81 (see FIG. 3).

If the operator 21 performs an operation by observing the observation part OP, such as a part to be treated, through the binocular stereo-microscope 40, the adapter lens 80 is removed from the holder H and the optical path length L is shortened (that is, an operating distance is shortened) as shown by the solid line in FIG. 1 so that an high-powered image of the observation part is formed on the solid state device 71a.

On the other hand, if the operator 21 performs it without the binocular stereo-microscope 40, the adapter frame 81 is connected to the lower portion of the holder H and then the tip of the locking screw 83 is engaged with the groove M to fit the adapter lens 80 on the holder H. As a result, the optical path length L for causing the solid state device 71a and the observation part OP to be conjugate with each other is lengthened (that is, the operating distance is lengthened) as shown by the stitch line in FIG. 1. And the supporting arm 34 is moved up to form a low-powered image of the observation part OP on the solid state device 71a.

A height-adjustable operating table (operating bed), not shown, is placed in the operating room. The observing position of the operator 21 depends on the height of the operating table and the distance (reaching distance) between the eyepiece of the microscope 40 and the observation part (part undergoing the operation or object point).

From such a viewpoint as mentioned above, the height of the operating table is preferably adjusted within the range of 700 mm to 1100 mm in order to obtain the most comfortable position of the operator 21. On the other hand, if the operator 21 performs it without the binocular stereo-microscope 40, the objective lens 51 is moved to be 1850 mm distant from the floor of the operating room so that the microscope 40 is not obstructive to the operation.

Therefore, as long as a back focal distance of a composite of the objective lens 51 and the concave lens 82 is set within the range of approximately 750 mm to 1150 mm, the microscope 40 will not be obstructive to the operation even if the microscope 40 is moved up.

This is expressed as follows:

$$\frac{1}{1150} < \frac{1}{f_\phi - D} + \frac{1}{f_A} < \frac{1}{750} \qquad (1)$$

where $f_\theta$ is the focal distance of the objective lens 51, $f_A$ is the focal distance of the concave lens 82, and D is the distance between the principal planes of the objective lens 51 and the concave lens 82. Therefore, the focal distance of the concave lens 82 is set so as to satisfying the inequality (1).

(Second Embodiment)

The method of changing the optical path length L is not necessarily limited to that of the first embodiment in which the back focal distance is set to a value within the range of 750 mm to 1150 mm by using the adapter lens (optical path length changing means) 80 to change the length L.

Figure 4:
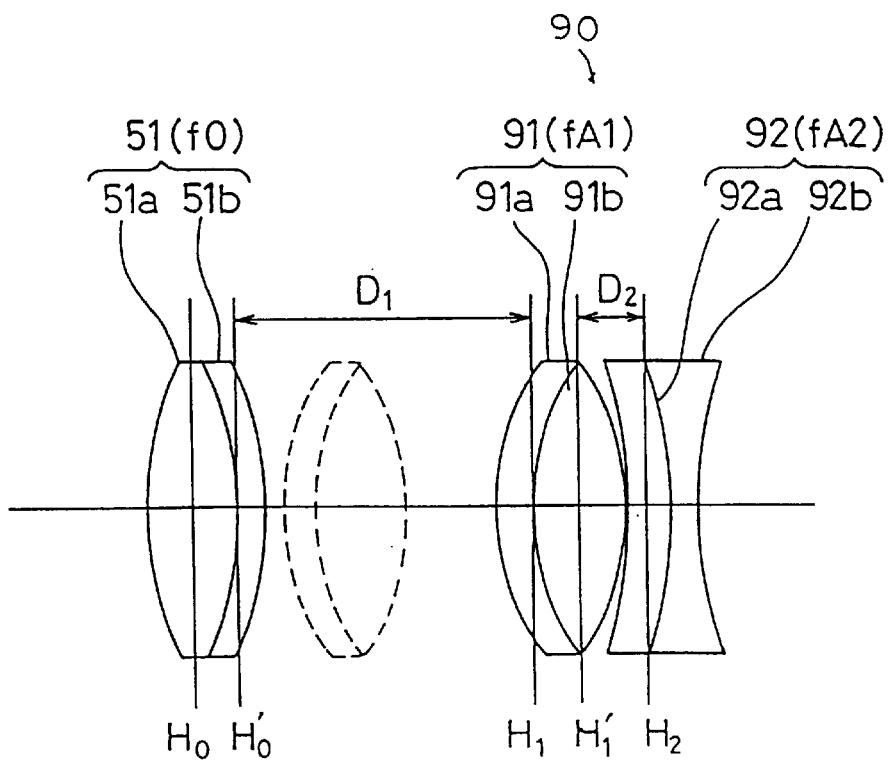
FIG. 4 is a descriptive drawing of a second embodiment of the medical microscopic system according to the invention.

For example, a method may be adopted in which an adapter lens 90 made up of a front group of lenses 91 and a back group of lenses 92 shown in FIG. 4 is fitted on the lower portion of the holder H and then the front group of lenses 91 is moved in the direction of the optical axis to consecutively change the back focal distance within the range of 750 mm to 1150 mm.

As shown in FIG. 4, the objective lens 51 is made up of lenses 51a and 51b, the front group of lenses 91 is made up of lenses 91a and 92b, and the back group of lenses 92 is made up of lenses 92a and 92b.

Let it be supposed that the principal planes of the lenses 51a and 51b are referred to by H0, H0', respectively, the principal planes of the lenses 91a and 91b are referred to by H1, H1', respectively, and the principal plane of the lens 92a is referred to by H2. The focal distance fA1 of the front group of lenses 91 and the focal distance fA2 of the back group of lenses 92 are obtained by the following simultaneous equations:

$$\frac{\frac{1}{f0} + \left(1 - \frac{D1}{f0}\right) \cdot \frac{1}{fA1}}{1 - \frac{D1}{f0} - \left\{\frac{1}{f0} + \left(1 - \frac{D1}{f0}\right)\right\} \cdot \frac{D2}{fA1}} + \frac{1}{fA2} = \frac{1}{1150} \qquad \text{Eq. (2)}$$

$$\frac{\frac{1}{f0} + \left(1 - \frac{D1'}{f0}\right) \cdot \frac{1}{fA1}}{1 - \frac{D1'}{f0} - \left\{\frac{1}{f0} + \left(1 - \frac{D1'}{f0}\right)\right\} \cdot \frac{D2'}{fA1}} + \frac{1}{fA2} = \frac{1}{750} \qquad \text{Eq. (2)'}$$

where D1 is the maximum distance between H0' and H1, D1' is the minimum distance between H0' and H1, D2 is the minimum distance between H1' and H2, D2' is the maximum distance between H1' and H2, and f0 is the focal distance of the lens 51. If f0=300, D1=25, D2=7, D1'=12, D2'=20, and D1+D2=D1'+D2'=32, the focal distance fA1 is equal to 200.792 and the focal distance fA2 is equal to −124.1.

(Third Embodiment)

Figure 5:
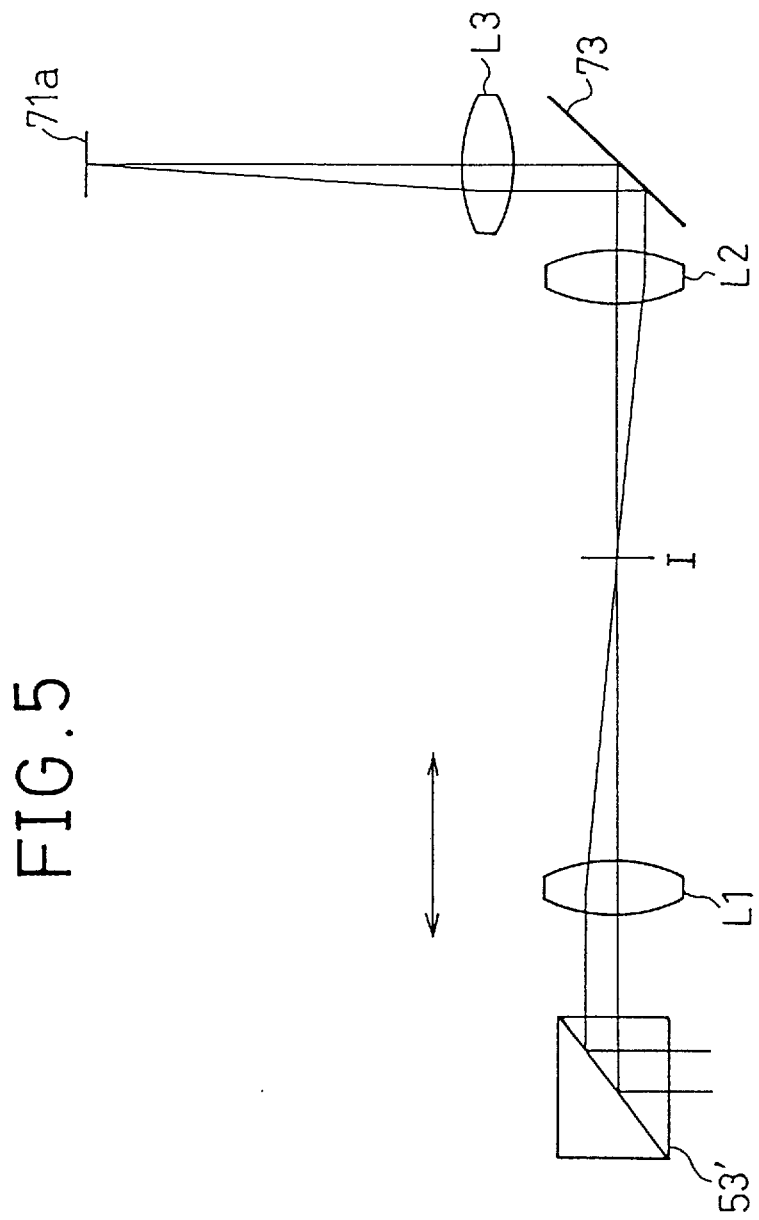
FIG. 5 is a descriptive drawing of a third embodiment of the medical microscopic system according to the invention.

FIG. 5 shows a third embodiment of the invention. In this embodiment, lenses L1 and L2, the focal distances of which are f1 and f2, respectively, are disposed between the beam splitter 53' and the oblique mirror 73. A set of the lenses L1 and L2 serves as a varifocal lens. Further, a lens L3 the focal distance of which is f3 is disposed between the oblique mirror 73 and the solid state photographing device 71a of the TV camera 71. The lens L1 is free to move in the direction of the optical axis and further is driven and controlled by a lens moving unit controlled by a controller (control circuit) 100 shown in FIG. 6.

The lens moving unit is made up of a moving system 101 shown in FIG. 6(a) and a driving apparatus 102 for driving the moving system 101. The moving system 101 includes a rotatable cam barrel 103 having a cam slit 103a in the spiral direction as shown in FIG. 6(b), a stationary barrel 104 having a guide slit 104a in the lengthwise direction as shown in FIGS. 6(a) and 6(b), a lens holding barrel 105 fitted in the cam barrel 103, and a guide pin 106 fixed to the lens holding barrel 105 through the slits 103a and 104a.

The driving apparatus 102 is made up of a pulse motor and a gear reduction system and is driven and controlled by the controller 100. The reference numeral 106a designates a switch operating member integrated with the guide pin 106.

When an on-signal is sent from the foot switch, the controller 100 actuates the driving apparatus 102 to drive the cam barrel 103 so that the lens L1 is moved to the beam splitter 53' by means of the cam slit 103a, the guide slit 104a, and the guide pin 106.

In the neighborhood of the stationary barrel 104 is disposed a microswitch MS for turning on when the lens L1 is moved more than a given distance (for example, 2.7 mm) in the direction opposite to the beam splitter 53'. When this signal is sent from the microswitch MS, the controller 100 halts the driving apparatus 102.

On the other hand, when an off-signal is sent from the foot switch FS, the controller 100 actuates the driving apparatus 102 to drive the cam barrel 103 so that the lens L1 is moved by a given distance in the direction opposite to the beam splitter 53' by means of the cam slit 103a, the guide slit 104a, and the guide pin 106.

In order to make the ratio of a visual field of the observation optical system 50 and the TV camera 71 100%, the focal distance of a relay portion on the side of the TV camera 71 is preferably set to 100 mm or so if the size of the solid state device 71a of the TV camera 71 is ⅔ inches.

If the relay portion on the side of the TV camera 71 is constructed as shown in FIG. 5, the focal distance f of the relay portion is expressed as follows:

$$f = f1 \cdot (f3/f2) \approx 100$$

If the focal distance of the objective lens 51 is referred to by f0, an on-the-path imaging plane of the lens L1 is referred to by I, and the zoom magnification of the variable power lens 52 (52') is referred to by r, the magnification from the on-the-path imaging plane I to the object point (observation part) is expressed by f0/f1·r. Accordingly, if the lens L1 or L2 is moved by a mm in the direction of the optical axis, the object point is displaced by a·(f0/f1·r)².

Therefore, a back focal distance to be required can be obtained by satisfying the following inequality:

$$750 < a \cdot (f0/f1 \cdot r)^2 + f0 < 1150 \qquad (3)$$

If f0=300 mm and r=0.4 (minimum), the inequality (3) is transformed as follows:

$$0.0008 f1^2 < a < 0.0015 f1^2 \qquad (4)$$

Further, if the maximum moving distance of the lens L1 or L2 is 5 mm, according to the inequality (4), the back focal distance is from 750 mm to 1150 mm within the range of 2.7 mm to 5 mm of a.

When an on-signal is sent from the foot switch FS, the controller 100 drives and controls a supporting post moving device 107 such as an oil pressure circuit. Thereby, the supporting post 32 is coarsely moved up by a given distance to adjust the microscope 40 coarsely. At the same time, the fine adjustment 41 is controlled to finely adjust the microscope 40 to the middle within its slight movement range.

On the other hand, when an off-signal is sent from the foot switch FS, the controller 100 drives and controls the supporting post moving device 107 so as to coarsely move the supporting post 32 down by a given distance and coarsely adjust the microscope 40. At the same time, the fine adjustment 41 is controlled to return the microscope 40 to the former position by means of the driver 108.

(Fourth Embodiment)

Figure 7:
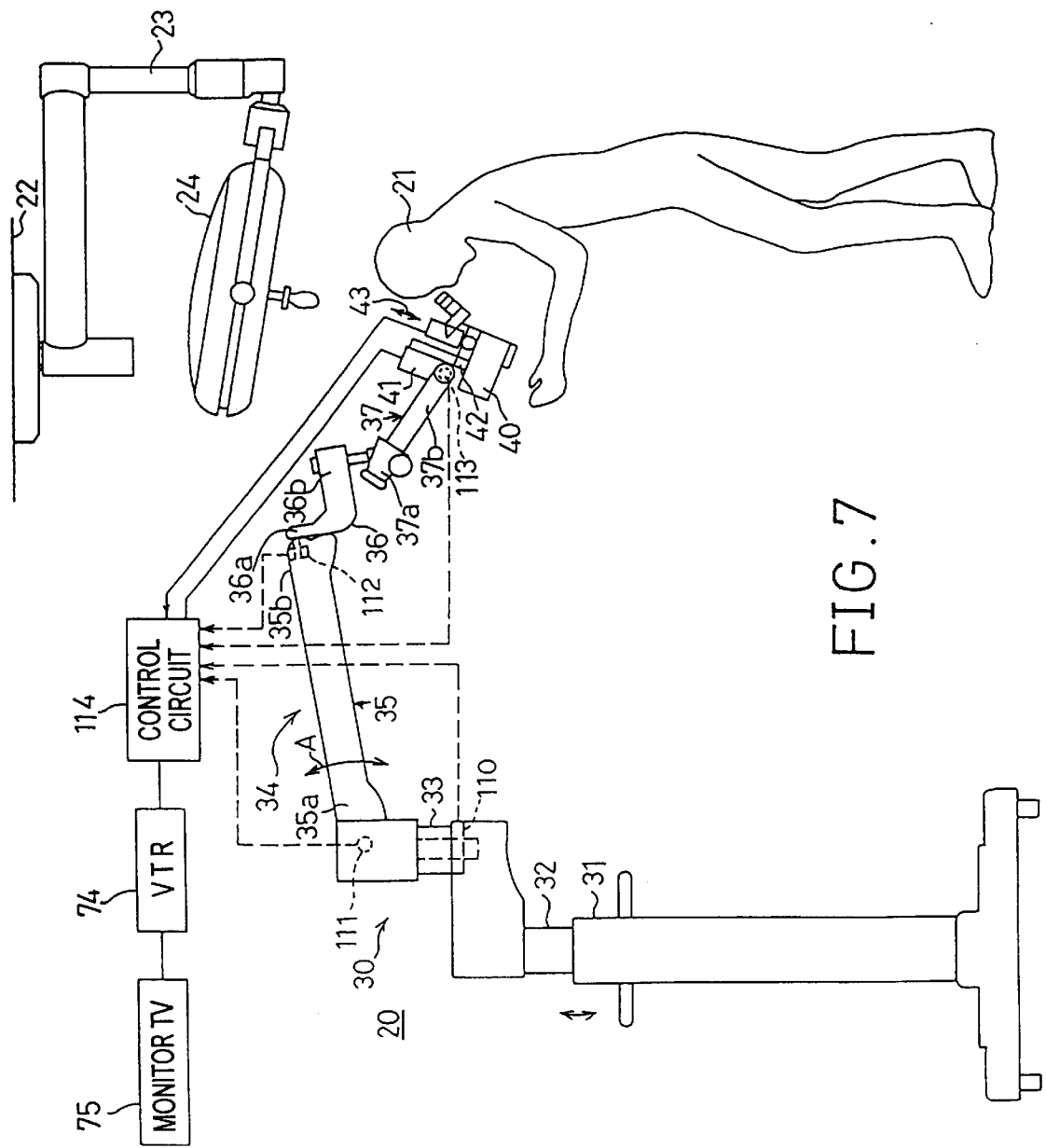
FIG. 7 is a descriptive drawing of a fourth embodiment of the medical microscopic system according to the invention.

FIG. 7 shows a fourth embodiment of the invention. In this embodiment, instead of the foot switch FS controlling the respective devices as shown in the sixth embodiment, the lens L1 is controlled according to the pivoting of the supporting arm 34.

As shown in FIG. 7, a rotary encoder 110 for detecting a horizontal rotational angle of the arm shaft 33 is disposed in the upper portion of the supporting post 32, a rotary encoder 111 for detecting a rotational angle of the arm 35 is disposed in the arm shaft 33, a rotary encoder 112 for detecting a rotational angle of the arm 36 is disposed in the free end portion of the arm 35, and a rotary encoder 113 for detecting a rotational angle of the fine adjustment 41 is disposed in the arm 37. Signals output by the rotary encoders 110 to 113 are input to the control circuit 114.

The control circuit 114 calculates a moved distance or position of the microscope 40 in the horizontal, upward, or downward direction based on the signals sent from the rotary encoders 110 to 113. If the microscope 40 is moved much more than a given distance away from the neighborhood of the part to be operated, the driving apparatus 102 is controlled so that the lens L1 is brought close to the beam splitter 53' by the actions of the cam barrel 103, the cam slit 103a, the guide slit 104a, and the guide pin 106.

On the other hand, if the microscope 40 is moved again close to the neighborhood of the part to be operated, the driving apparatus 102 is controlled so that the lens L1 goes away from the beam splitter 53' by the actions of the cam barrel 103, the cam slit 103a, the guide slit 104a, and the guide pin 106.

(Fifth Embodiment)

Figure 8:
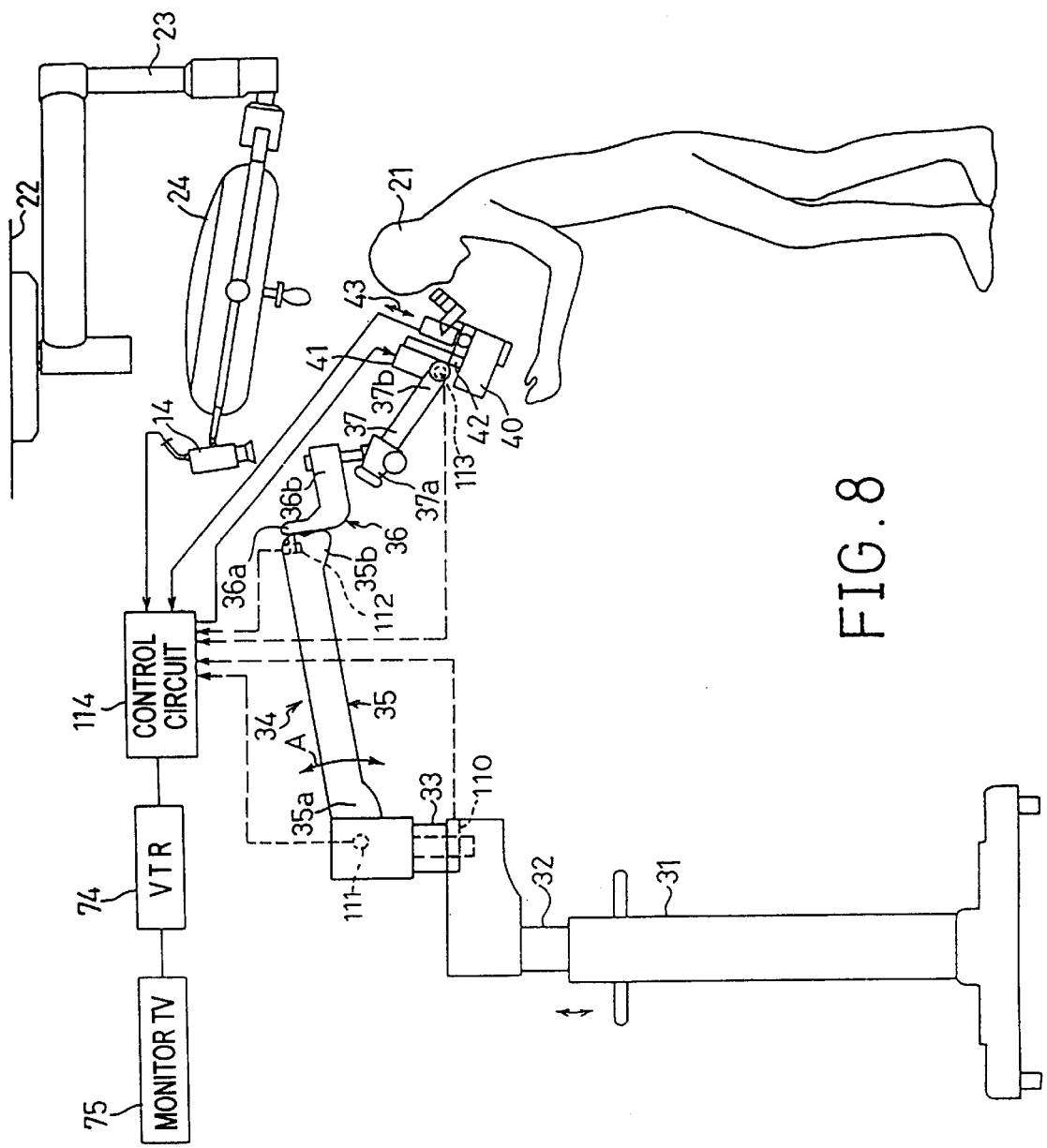
FIG. 8 is a descriptive drawing of a fifth embodiment of the medical microscopic system according to the invention.

FIG. 8 shows a fifth embodiment of the invention. In this embodiment, the shadow-free operating lamp 24 shown in FIG. 7 is provided with a TV camera. Image signals sent from this TV camera 14 and the TV camera (not shown) of the microscope 40 are controlled by the control circuit 114 and then they are input to the VTR 74 and the monitor TV 75.

The control circuit 114 calculates a moved distance or position of the microscope 40 in the horizontal, upward, or downward direction based on the signals sent from the rotary encoders 110 to 113. If the microscope 40 is close to the neighborhood of the part to be operated, the control circuit 114 inputs the image signal sent from the TV camera (not shown) of the microscope 40 to the VTR 74 and the monitor TV.

On the other hand, if the microscope 40 is kept more than a given distance away from the neighborhood of the part to be operated, the control circuit 114 inputs the image signal sent from the TV camera 14 of the operating lamp 24 to the VTR 74 and the monitor TV.

Figure 12:
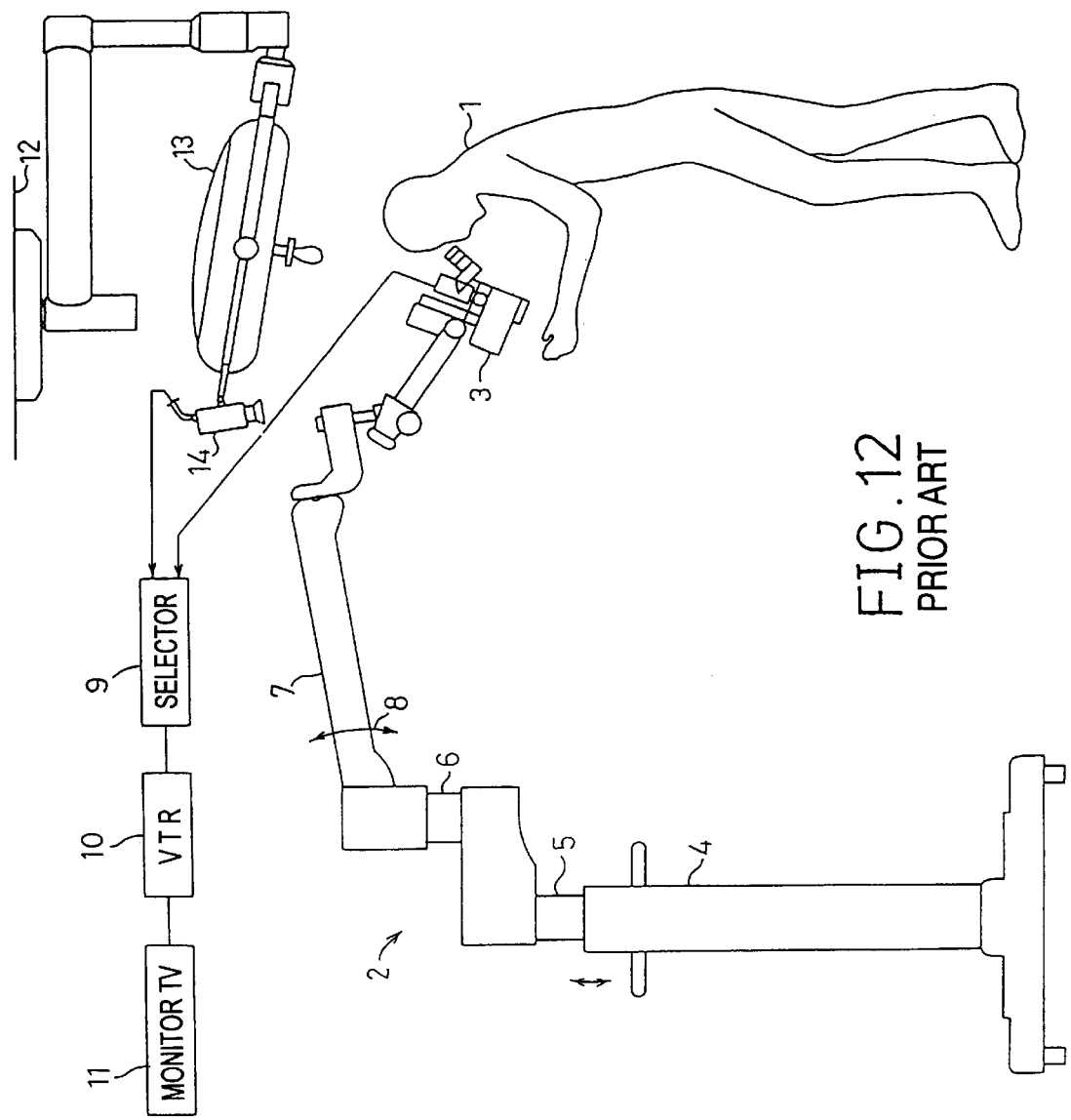
FIG. 12 is a descriptive drawing of an example of a conventional medical microscopic system.

Further, if the microscope 40 is moved again close to the neighborhood of the part to be operated, the control circuit 114 inputs the image signal sent from the TV camera (not shown) of the microscope 40 to the VTR 74 and the monitor TV. The binocular stereo-microscope 40 may be replaced with the binocular stereo-microscope 3 shown in FIG. 12.

Instead of the encoders 110 to 113 shown in FIGS. 7 and 8, potentiometers may be used to detect the moved distances or rotational angles of the respective arms.

(Sixth Embodiment)

Figure 9:
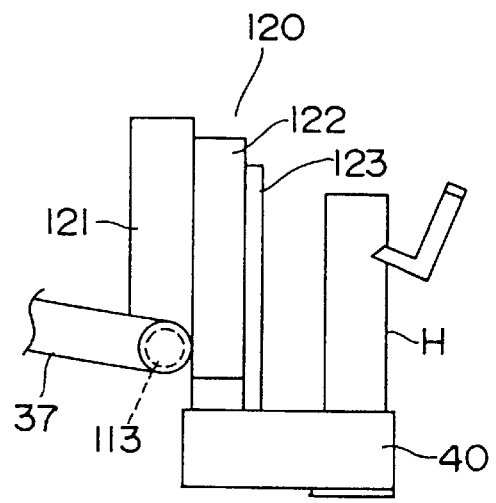
FIG. 9 is a descriptive drawing of a sixth embodiment of the medical microscopic system according to the invention.
Figure 10:
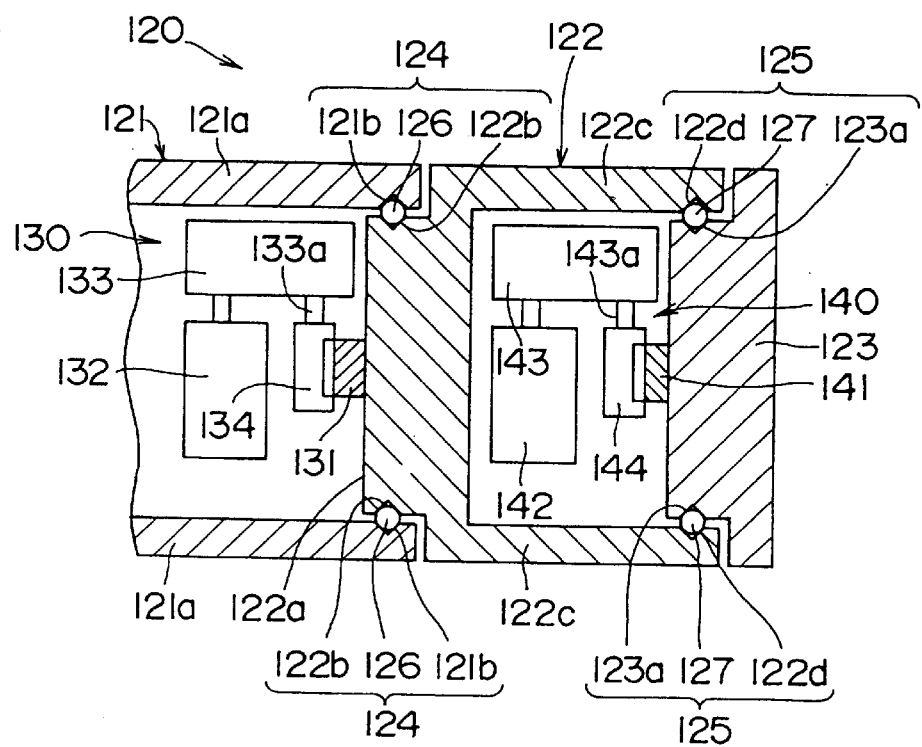
FIG. 10 is a horizontal sectional view of FIG. 9.
Figure 11:
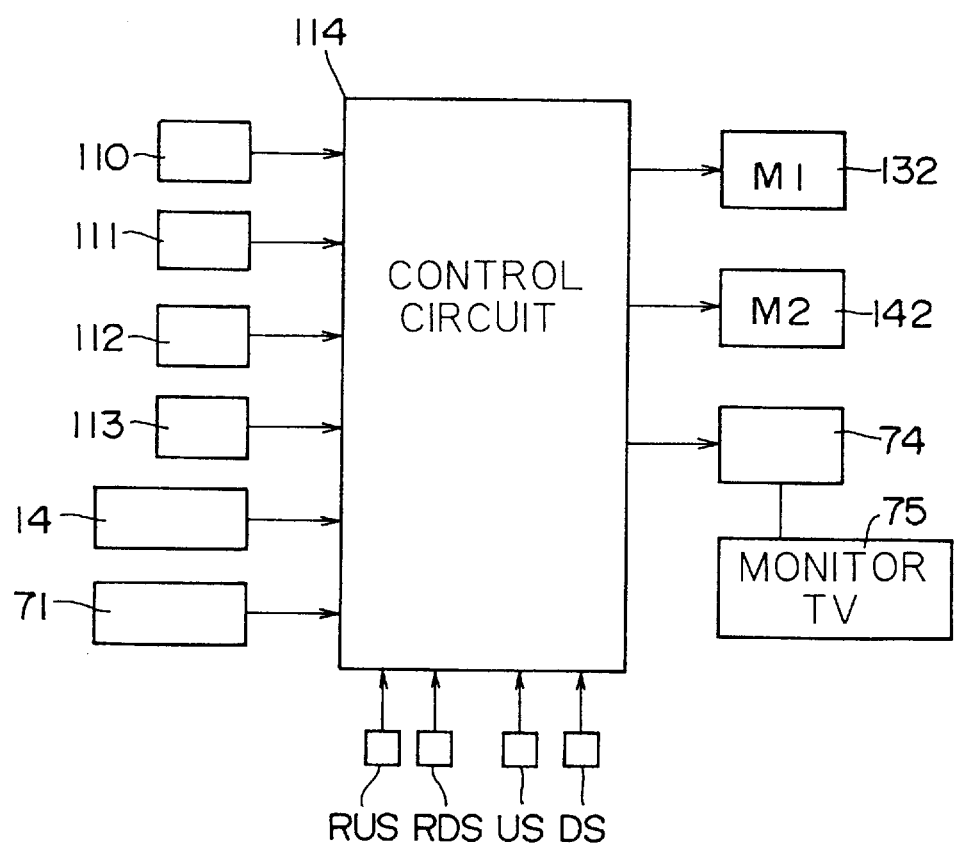
FIG. 11 is a diagram of a control circuit of the medical microscopic system of FIGS. 9 and 10.

FIGS. 9 to 11 show a sixth embodiment of the invention. In this embodiment, the fine adjustment 41 mentioned above is replaced with an apparatus 120 for elevating and lowering the microscope 40 coarsely and finely. Image signals sent from the TV cameras 14 and 71 to the VTR 74 is switched according to the motion of the elevating and lowering apparatus 120.

As shown in FIG. 9, the elevating and lowering apparatus 120 is made up of a pivoting box 121, a sliding box 122, and a supporting plate 123. The pivoting box 121 is joined to the end portion of the arm 37 so as to pivot freely in the vertical plane. The sliding box 122 is joined to the pivoting box 121 by means of a sliding mechanism 124 so as to slide freely. The supporting plate 123 is joined to the sliding box 122 by means of a sliding mechanism 125 so as to move up and down freely. The rotational angle of the pivoting box 121 is detected by the rotary encoder 113. The binocular stereo-microscope 40 is fixed to the lower end of the supporting plate 123.

As shown in FIG. 10, the sliding mechanism 124 comprises V-shaped grooves 121b, 121b formed in the side walls 121a, 121a of the pivoting box 121 opposite to each other, V-shaped grooves 122b, 122b opposite to the V-shaped grooves 121b, 121b respectively and formed in the convex portion 122a of the sliding box 122, and balls 126, 126 each placed between the grooves 121b and 122b.

Also, the sliding mechanism 125 comprises V-shaped grooves 122d, 122d formed in the side walls 122c, 122cof the sliding box 122 opposite to each other, V-shaped grooves 123a, 123a opposite to the V-shaped grooves 122d, 122d respectively and formed in the convex portion of the supporting plate 123, and balls 127, 127 each placed between the grooves 122d and 123a.

The elevating and lowering apparatus 120 further includes a coarse adjustment 130, disposed in the pivoting box 121, for adjusting the microscope 40 coarsely and a fine adjustment 140, disposed in the sliding box 122, for adjusting the microscope 40 finely.

The coarse adjustment 130 is made up of a rack 131 fixed to the convex portion 122a of the sliding box 122, a pulse motor 132 fixed in the pivoting box 121 for coarse adjustment, a gear reduction system 133 linked to the pulse motor 132, and a pinion 134 integrated with an output shaft 133a of the gear reduction system 133 and engaged with the rack 131.

Also, the fine adjustment 140 is made up of a rack 141 fixed to the supporting plate 123, a pulse motor 142 fixed in the sliding box 122 for fine adjustment, a gear reduction system 143 linked to the pulse motor 142, and a pinion 144 integrated with an output shaft 143a of the gear reduction system 143 and engaged with the rack 141.

As shown in FIG. 11, when an operating signal is sent from a switch RUS for coarse adjustment, the control circuit 114 normally drives the pulse motor 132 to coarsely move the rack 131 upward by the pinion 134. Also, when an operating signal is sent from a switch RDS for coarse adjustment, the control circuit 114 inversely drives the pulse motor 132 to coarsely move the rack 131 downward by the pinion 134. When the rack 131 is coarsely moved upward or downward, the sliding box 122, the supporting plate 123, and the microscope 40 are also coarsely moved according to the motion of the rack 131.

On the other hand, when an operating signal is sent from a switch US for fine adjustment, the control circuit 114 normally drives the pulse motor 132 to finely move the rack 131 upward by the pinion 134. Also, when an operating signal is sent from a switch DS for fine adjustment, the control circuit 114 inversely drives the pulse motor 132 to finely move the rack 131 downward by the pinion 134. When the rack 131 is finely moved upward or downward, the sliding box 122, the supporting plate 123, and the microscope 40 are also finely moved according to the motion of the rack 131.

If the control circuit 114 receives the operating signal from the switch RUS or RDS for coarse adjustment while the image signal of the TV camera (first photographing means) 71 is input to the VTR 74 and the observation part is displayed on the monitor TV 75, the control circuit 114 stops the input of the image signal from the TV camera 71 to the VTR 74 and causes the image signal of the TV camera (second photographing means) 14 fixed to the operating lamp 24 to be input to the VTR 74 in order to display the whole of the observation part on the monitor TV 75.

On the other hand, if the control circuit 114 receives the operating signal from the switch RUS or RDS for coarse adjustment while the image signal of the TV camera (second photographing means) 14 is input to the VTR 74 and the whole of the observation part is displayed on the monitor TV 75, the control circuit 114 stops the input of the image signal from the TV camera 14 to the VTR 74 and causes the image signal of the TV camera (first photographing means) 74 of the microscope 40 to be input to the VTR 74 in order to display the magnified image of one portion of the observation part on the monitor TV 75.

(Seventh Embodiment)

Figure 6:
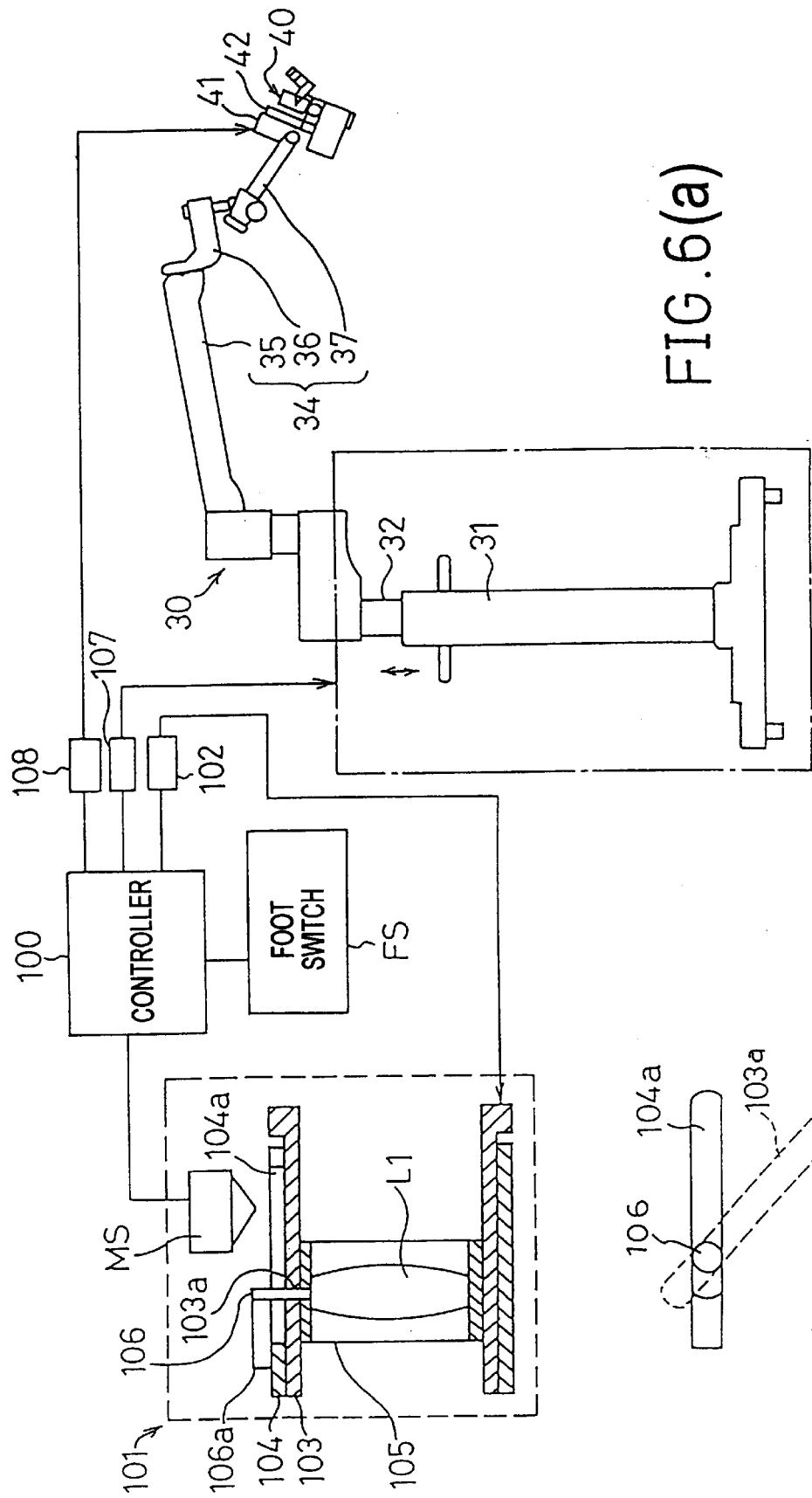
FIG. 6(a) is a descriptive drawing of a control system of the medical microscopic system of FIG. 5.
FIG. 6(b) is a plane development of a spiral cam slit for a rotatable cam barrel shown in FIG. 6(a).

The control circuit 114 shown in FIG. 8 may be provided with the function of the controller 100 shown in FIG. 6 and further the arrangement in FIG. 6 may be combined with the embodiment in FIG. 8. If combined so, the switching of the image by the control circuit 114 is performed as follows.

When the control circuit 114 receives an on- or off-signal of the foot switch FS for operating the supporting post moving device (coarse adjustment) 107, the image signal of the TV camera (first photographing means) 71 is switched to the image signal of the TV camera (second photographing means) 14 and then the latter signal is input to the VTR 74 as an image signal processing device, so that the whole of the observation part is displayed on the monitor TV 75.

On the other hand, when the control circuit 114 receives an operating signal of the fine adjustment 41, the image signal of the TV camera (second photographing means) 14 is switched to the image signal of the TV camera (first photographing means) 71 and then the latter signal is input to the VTR 74, so that the magnified image of one portion of the observation part, such as a part to be treated, is displayed on the monitor TV 75.

(Eighth Embodiment)

The switching of the image by means of the control circuit 114 is not necessarily limited to that in the seventh embodiment.

For example, the control circuit 114 shown in the seventh embodiment may switch the image signals of the TV cameras 71, 14 (first and second photographing means, respectively) based on each amount of movement of the supporting post 32 and the supporting arm 34, that is, based on an amount of movement of the microscope 40 after a given time (for example, several seconds to on the order of ten seconds) has elapsed since the control circuit 114 received the on-signal of the foot switch FS. In this case, the amount of movement of the microscope 40 may be calculated from the time during which the supporting post moving device (coarse adjustment) 107 was driven or may be calculated from the amount of movement of the supporting post 32 detected by the output change of a linear sensor, such as a Magnescale (registered trademark) or an optoelectronic linear encoder, disposed between the column 31 and the supporting post 32.

What is claimed is:

1. A medical microscope system comprising:

an operation microscope including an observation optical system for observing an image of a part of a subject, and an electronic photographing optical system for branching a beam of light incident on said observation optical system from said part of the subject by a branching means disposed in an optical path of said observation optical system and thereafter guiding a branched beam of light to a first electronic photographing means for transmitting image signals and conjugated with said part of the subject;

a supporting device for supporting said operation microscope so as to be movable forward, rearward, rightward, leftward, upward and downward;

a second electronic photographing means for transmitting image signals and disposed on a ceiling of an operation room;

an image signal processing unit for processing the image signals transmitted from said first and second electronic photographic means;

detecting means for detecting an amount of movement of said supporting device; and a control circuit for switching over the transmitted image signals and inputting either of said image signals to said image signal processing unit based on a detection signal of said detecting means.

2. The medical microscope system of claim 1, wherein said detecting means is attached to said supporting device to detect a a position of movement in upward and downward directions of said operation microscope.

3. The medical microscope system of claim 2, wherein said supporting device comprises a supporting member and a supporting arm having one end supported by said supporting member so that the supporting arm is pivoted in upward and downward directions, and said detecting means is mounted between the one end of said supporting arm and said supporting member.

4. The medical microscope system of claim 1, wherein said supporting arm is an articulated arm comprising a plurality of arm segments pivotally connected to each other, and a joint for each arm segment, the joint being provided with a detecting means for determining a position of movement of said supporting arm, based on an amount of pivotal movement of each arm segment.

5. The medical microscope system of claim 4, wherein said detecting means is one of a rotary encoder and a potentiometer.

6. The medical microscope system of claim 1, wherein said supporting device comprises a supporting arm for supporting said operation microscope and a driving means controlled by said control circuit to drive said supporting arm in upward and downward directions.

7. The medical microscope system of claim 6, wherein said control circuit switches over from the image signal transmitted from said first electronic photographing means to the image signal transmitted from said second photographing means, based on a drive operation signal transmitted from said driving means, and inputs the image signal transmitted from said second electronic photographing means to said image processing unit, whereby a whole image of said part of the subject is observed, whereas said control circuit switches over from the image signal transmitted from said second electronic photographing means to the image signal transmitted from said first electronic photographing means, based on a drive operation signal transmitted from said driving means, and inputs the image signal transmitted from said first electronic photographing means to said image signal processing unit.

8. The medical microscope system of claim 1, wherein said supporting device comprises supporting means moveable in upward and downward directions, a coarse adjustment device controlled by said control circuit, based on an on-off signal of a foot switch, for driving said supporting means upward and downward, and a fine adjustment device for supporting and moving said supporting post slightly upward and downward.

9. The medical microscope system of claim 8, wherein said control circuit switches over from the image signal transmitted from said first electronic photographing means to the image signal transmitted from said second photographing means, based on the on-off signal of said foot switch, and inputs the image signal transmitted from said second electronic photographing means to said image processing unit, whereby a whole image of said part of the subject is observed, whereas said control circuit switches over from the image signal transmitted from said second electronic photographing means to the image signal transmitted from said first electronic photographing means, based on an operation signal of said fine adjustment device, and inputs the image signal transmitted from said first electronic photographing means to said image signal processing unit, whereby an image of said part of the subject is magnified.

10. The medical microscope system of claim 1, wherein said supporting device comprises a supporting post moveable upward and downward, a post driving means controlled by said control circuit for driving said supporting post upward and downward, and a supporting arm attached to an upper end part of said supporting post.

11. The medical microscope system of claim 10 including a foot switch, and wherein when said foot switch is turned on, said control circuit controls said post driving means to raise said supporting post, whereby said operating microscope is moved upward by a predetermined coarse distance, whereas when said foot switch is turned off, said control circuit controls said post driving means to lower said supporting post so that said operation microscope is moved downward by the predetermined coarse distance.

12. The medical microscope system of claim 11, wherein said first and second electronic photographing means are switched over to each other based on an on-off operation of said foot switch.

13. The medical microscope system of claim 11, wherein an amount of positional change of said coarse adjustment device is detected upon a given time lapse after said foot switch is turned on, and said first and second electronic photographing means are switched over to each other based on the amount of the given time lapse.

* * * * *